United States Patent
Hogwood et al.

(10) Patent No.: US 10,850,051 B2
(45) Date of Patent: Dec. 1, 2020

(54) AEROSOL-GENERATING SYSTEM COMPRISING A RUPTURING PORTION

(71) Applicant: Philip Morris Products S.A., Neuchatel (CH)

(72) Inventors: Jonathan Hogwood, Royston (GB); Stuart Michael Ruan Jones, Royston (GB); John Antony Stephenson, Cambridge (GB); David Edington, St Albans (GB); Christopher Coulson, London (GB)

(73) Assignee: Philip Morris Products S.A., Neuchatel (CH)

( * ) Notice: Subject to any disclaimer, the term of this patent is extended or adjusted under 35 U.S.C. 154(b) by 399 days.

(21) Appl. No.: 15/557,827

(22) PCT Filed: Mar. 24, 2016

(86) PCT No.: PCT/EP2016/056575
§ 371 (c)(1),
(2) Date: Sep. 13, 2017

(87) PCT Pub. No.: WO2016/156214
PCT Pub. Date: Oct. 6, 2016

(65) Prior Publication Data
US 2018/0289905 A1 Oct. 11, 2018

(30) Foreign Application Priority Data
Mar. 27, 2015 (EP) ..................... 15161531

(51) Int. Cl.
*A61M 15/00* (2006.01)
*A24F 47/00* (2020.01)
(Continued)

(52) U.S. Cl.
CPC .......... *A61M 15/0041* (2014.02); *A24F 7/00* (2013.01); *A24F 47/008* (2013.01);
(Continued)

(58) Field of Classification Search
CPC .......... A61M 15/0041; A61M 15/0038; A61M 11/042; A61M 15/0021; A61M 15/06;
(Continued)

(56) References Cited

U.S. PATENT DOCUMENTS 5,595,175 A 1/1997 Malcher et al.
10,085,482 B2 * 10/2018 Silvestrini .............. A24B 15/16
(Continued)

FOREIGN PATENT DOCUMENTS

CN 2657881 Y 11/2004
CN 2789614 Y 6/2006
(Continued)

OTHER PUBLICATIONS

Extended European Search Report dated Sep. 11, 2017 in Patent Application No. 15161531.7.
(Continued)

*Primary Examiner* — Timothy A Stanis
*Assistant Examiner* — Arielle Wolff
(74) *Attorney, Agent, or Firm* — Oblon, McClelland, Maier & Neustadt, L.L.P.

(57) ABSTRACT

An aerosol-generating system is provided, including an aerosol-generating device including a heater element, and an aerosol-generating article configured to engage with the aerosol-generating device, the aerosol-generating article including a medicament source, a volatile delivery enhancing compound source, and at least one frangible barrier sealing the medicament source and the volatile delivery enhancing compound source, the aerosol-generating system further including a rupturing portion forming part of the
(Continued)

aerosol-generating device or the aerosol-generating article, the aerosol-generating system being configured to allow relative sliding movement between the rupturing portion and the at least one frangible barrier to rupture the at least one frangible barrier.

2 Claims, 4 Drawing Sheets

(51) Int. Cl.
*A61M 15/06* (2006.01)
*A61M 11/04* (2006.01)
*A24F 7/00* (2006.01)

(52) U.S. Cl.
CPC ...... *A61M 11/042* (2014.02); *A61M 15/0021* (2014.02); *A61M 15/0038* (2014.02); *A61M 15/06* (2013.01); *A61M 2205/3368* (2013.01); *A61M 2205/3653* (2013.01); *A61M 2205/8206* (2013.01)

(58) Field of Classification Search
CPC .. A61M 2205/3368; A61M 2205/3653; A61M 2205/8206; A61M 15/16; A61M 11/04; A61M 11/041; A61M 11/044; A61M 11/045; A61M 11/047; A61M 11/048; A24F 7/00; A24F 47/008; A24F 47/00; A24F 47/002; A24F 47/004; A24F 47/006
See application file for complete search history.

(56) References Cited

U.S. PATENT DOCUMENTS

| | | | |
|---|---|---|---|
| 2014/0000638 A1 | 1/2014 | Sebastian et al. | |
| 2016/0021932 A1 | 1/2016 | Silvestrini et al. | |
| 2016/0029694 A1 | 2/2016 | Clements et al. | |

FOREIGN PATENT DOCUMENTS

| | | | | |
|---|---|---|---|---|
| CN | 106455723 A | | 2/2017 | |
| DE | 102006006647 B3 | * | 1/2007 | .......... A61M 15/004 |
| EP | 2 082 760 A1 | | 7/2009 | |
| JP | 2009-213428 A | | 9/2009 | |
| JP | 2014-527835 A | | 10/2014 | |
| RU | 2 309 419 C2 | | 5/2010 | |
| WO | WO 2008/121610 A1 | | 10/2008 | |
| WO | 2008/139490 A2 | | 11/2008 | |
| WO | WO 2010/107613 A1 | | 9/2010 | |
| WO | WO 2011/034723 A1 | | 3/2011 | |
| WO | WO 2014/139611 A1 | | 9/2014 | |
| WO | WO 2014/140087 A1 | | 9/2014 | |
| WO | WO 2014/140320 A1 | | 9/2014 | |
| WO | WO 2014/187770 A2 | | 11/2014 | |
| WO | WO 2015/000974 A1 | | 1/2015 | |
| WO | WO 2015/082652 A1 | | 6/2015 | |

OTHER PUBLICATIONS

Combined Chinese Office Action and Search Report dated Dec. 24, 2019, in Patent Application No. 201680014470.0 (with English translation), citing documents AA and AO-AR therein, 19 pages.
Office Action dated Apr. 26, 2019 in Russian Patent Application No. 2017133232, citing document AO therein, 15 pages (with English translation).
International Search Report and Written Opinion dated Jun. 14, 2016 in PCT/EP2016/056575, filed Mar. 24, 2016.
Japanese Office Action dated Jun. 1, 2020 in Patent Application No. 2017-548387 (with English translation), 6 pages.
Chinese Office Action and Search Report dated Jul. 29, 2020 in corresponding Chinese Patent Application No. 201680014470.0 (with English translation), 20 pages.

* cited by examiner

AEROSOL-GENERATING SYSTEM COMPRISING A RUPTURING PORTION

The present invention relates to an aerosol-generating system for generating an aerosol comprising a medicament. The invention finds particular application as an aerosol-generating system for generating an aerosol comprising nicotine salt particles.

Some devices for delivering nicotine or other medicaments to a user comprise a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. Therefore, to prevent premature evaporation of the volatile delivery enhancing compound and the nicotine both sources are usually sealed with one or more frangible seals that a user must break to use the aerosol-generating system. However, it may be difficult to provide a frangible seal that can be reliably and consistently broken by a user to provide a consistent user experience. Accordingly, it would be desirable to provide a device comprising nicotine or other medicament source and a volatile delivery enhancing compound source that alleviates these difficulties.

The present invention provides an aerosol-generating system comprising an aerosol-generating device comprising a heater element, and an aerosol-generating article configured to engage with the aerosol-generating device. The aerosol-generating article comprises a medicament source, a volatile delivery enhancing compound source, and at least one frangible barrier sealing the medicament source and the volatile delivery enhancing compound source. The aerosol-generating system also comprises a rupturing portion forming part of the aerosol-generating device or the aerosol-generating article, wherein the aerosol-generating system is configured to allow relative sliding movement between the rupturing portion and the at least one frangible barrier to rupture the at least one frangible barrier.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. The aerosol-generating article may comprise an aerosol-forming substrate capable of releasing upon heating volatile compounds, which can form an aerosol. An aerosol-generating article may be entirely consumable and mainly comprise a medicament source and a volatile delivery enhancing compound. Alternatively, an aerosol-generating article may comprise a reusable portion, such as a mouthpiece configured for attachment to an aerosol-generating device, and a consumable portion comprising the medicament and volatile delivery enhancing compound sources and configured for insertion into the reusable portion.

As used herein, the term "aerosol-generating system" refers to a combination of an aerosol-generating article with an aerosol-generating device.

As used herein, the term "medicament source" refers to a source of one or more volatile compounds intended for delivery to the lungs of a user. Preferably, the medicament source comprises a nicotine source.

As used herein, the term "volatile delivery enhancing compound source" refers to a source of one or more volatile compounds that react with the medicament source in the gas phase to aid delivery of the one or more compounds from the medicament source to the user.

By providing an integrated rupturing portion as part of one of the aerosol-generating device and the aerosol-generating article, an aerosol-generating system in accordance with the present invention can provide a convenient and reliable means for a user to break the at least one frangible barrier prior to using the aerosol-generating system.

In a first set of embodiments, the aerosol-generating article comprises a housing, wherein the medicament source and the volatile delivery enhancing compound source are contained within the housing, and the rupturing portion is slidably mounted on the housing and arranged so that sliding the rupturing portion along the housing ruptures the at least one frangible barrier.

In such embodiments, the rupturing portion may comprise a cutting element extending into an interior of the aerosol-generating article inside the housing. An activation element, such as a push button, may be connected to the cutting element and may extend through an elongate aperture in the housing, wherein in use a user can push on the activation element to slide the rupturing portion along the elongate aperture in the housing. The cutting element may comprise one or more cutting blades attached to or formed integrally with a carrier element arranged to slide within or adjacent to the elongate aperture in the housing. The activation element may be formed integrally with all or a portion of the cutting element, or the activation element may be formed separately and attached to the cutting element.

Preferably, the medicament source and the volatile delivery enhancing compound source are arranged in series within the aerosol-generating article and each comprise an elongate slot extending along a surface of the medicament source and the volatile delivery enhancing compound source, and wherein the cutting element of the rupturing portion is arranged to slide through the elongate slots in the medicament source and the volatile delivery enhancing compound source when the rupturing portion slides along the elongate aperture in the housing.

In a second set of embodiments, the aerosol-generating article may comprise a housing configured for attachment to the aerosol-generating device at an upstream end of the housing, wherein the medicament source and the volatile delivery enhancing compound source are contained within the housing. A mouthpiece may be slidably received within a downstream end of the housing and may comprise the rupturing portion. The mouthpiece may be arranged so that sliding the mouthpiece into the housing ruptures the at least one frangible barrier with the rupturing portion.

In such embodiments, the heater element may comprise an elongate heater element, wherein the aerosol-generating article comprises a resilient member positioned within the housing. The medicament source and the volatile delivery enhancing compound source may be provided on the resilient member, and the mouthpiece may be configured so that sliding the mouthpiece into the housing biases the resilient member against the elongate heater element when the aerosol-generating article is engaged with the aerosol-generating device. In these embodiments, the single sliding action of the mouthpiece advantageously performs a dual function. Sliding the mouthpiece into the housing may rupture the at least one frangible barrier and may bias the resilient member against the heater element.

In a third set of embodiments, the aerosol-generating article may comprise a consumable comprising a first wall portion on which the medicament source and the volatile delivery enhancing compound source are provided, and a second wall portion comprising the rupturing portion and connected to the first wall portion for relative sliding movement between the first and second wall portions. In such embodiments, the at least one frangible barrier may be provided between the first and second wall portions. The aerosol-generating article may further comprise a mouthpiece configured for attachment to the aerosol-generating device and comprising an aperture for receiving the consumable. The aerosol-generating article may be configured so that inserting the consumable into the aperture in the mouthpiece results in relative movement between the first and second wall portions so that the rupturing portion ruptures the at least one frangible barrier.

In these embodiments, the heater element may comprise an elongate heater element, wherein the aerosol-generating article comprises a resilient member positioned within the mouthpiece. The aerosol-generating article may be configured so that inserting the consumable into the mouthpiece biases the resilient member against the elongate heater element when the mouthpiece is attached to the aerosol-generating device. In these embodiments, the single action of sliding the consumable into the mouthpiece advantageously performs a dual function. Sliding the consumable into the mouthpiece may rupture the at least one frangible barrier and may bias the resilient member against the heater element.

In a fourth set of embodiments, the aerosol-generating article may comprise a housing configured for attachment to the aerosol-generating device at an upstream end of the housing and a rigid element positioned within the housing. The aerosol-generating article may further comprise a mouthpiece comprising a carrier element extending from the mouthpiece, wherein the medicament source and the volatile delivery enhancing compound source are provided on the carrier element. The aerosol-generating article may be configured to slidably receive the carrier element within the housing. Sliding the carrier element into the housing may compress the at least one frangible barrier between the carrier element and the rupturing portion comprising at least one of the rigid element and the heater element so that the at least one frangible barrier is ruptured. For example, the at least one frangible barrier may comprise a first blister containing the medicament and a second blister containing the volatile delivery enhancing compound. Upon insertion of the carrier element into the housing, each blister may be crushed and ruptured between the carrier element and one of the rigid element and the heater element.

As will be appreciated, any feature described above with reference to a set of embodiments of the present invention may also, where appropriate, be applicable to other embodiments of the invention.

As will be appreciated, any feature describe below is typically applicable to any of the embodiments described above.

The medicament source and the volatile delivery enhancing compound source may comprise a liquid sorbed onto a sorption element. The at least one frangible barrier may be formed from a sheet material wrapped around one or both of the sources or extending across an opening in aerosol-generating article. The sheet material may be formed from a metal foil or film.

The medicament and the volatile delivery enhancing compound may each comprise a liquid contained within a blister, wherein the blisters form the medicament source and the volatile delivery enhancing compound source. Each blister may be formed from a non-permeable material, such as a plastic, and each blister may form a frangible barrier sealing the medicament or the volatile delivery enhancing compound.

The rupturing portion may have any suitable shape and form for rupturing the at least one frangible barrier. Additionally, or alternatively, the at least one rupturing portion may be formed from any suitable material. Preferably, the at least one rupturing portion is formed from a rigid material, such as a plastic or a metal. Preferably, the at least one rupturing portion is sufficiently rigid such that it can rupture the at least one frangible barrier with substantially no deformation of the at least one rupturing portion.

The medicament source and the volatile delivery enhancing compound source are preferably arranged in series within the aerosol-generating article.

As used herein, by "series" it is meant that the medicament source and the volatile delivery enhancing compound source are arranged within the aerosol-generating article so that in use an air stream drawn through the aerosol-generating article passes through one of the medicament source and the volatile delivery enhancing compound source and then passes through the other of the medicament source and the volatile delivery enhancing compound source.

The medicament source and the volatile delivery enhancing compound source may be arranged in parallel within the aerosol-generating article.

Preferably, the medicament source is upstream of the volatile delivery enhancing compound source. In use of this configuration, preferably medicament vapour is released from the medicament source into the air stream drawn through the aerosol-generating article and volatile delivery enhancing compound vapour is released from the volatile delivery enhancing compound source into the medicament-containing air stream drawn through the aerosol-generating article, and the medicament vapour reacts with the volatile delivery enhancing compound vapour in the gas phase to form an aerosol, which is delivered to a user.

The volatile delivery enhancing compound preferably has a vapour pressure of at least about 20 Pa, more preferably at least about 50 Pa, more preferably at least about 75 Pa, most preferably at least 100 Pa. Unless otherwise stated, all vapour pressures referred to herein are vapour pressures at 25° C. measured in accordance with ASTM E1194-07.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination may have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

The volatile delivery enhancing compound may comprise one or more non-volatile compounds and one or more volatile compounds. The volatile delivery enhancing compound may comprise a solution of one or more non-volatile compounds in a volatile solvent or a mixture of one or more non-volatile liquid compounds and one or more volatile liquid compounds.

Preferably, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid. The volatile delivery enhancing compound may comprise lactic acid. Other suitable acids includes aspartic acid, glutamic acid, salicylic acid, tartaric acid, gallic acid, levulinic acid, acetic acid, malic acid, citric acid, oxalic acid, sulphuric acid, palmitic acid, and alginic acid. Preferably, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. Preferably, the volatile delivery enhancing compound comprises pyruvic acid.

Preferably, the volatile delivery enhancing compound source comprises a sorption element and a volatile delivery enhancing compound sorbed on the sorption element. The volatile delivery enhancing compound may be sorbed onto the sorption element during manufacture and the sorption element may be sealed. The volatile delivery enhancing compound may be stored separately from the sorption element, for example in a blister on or adjacent the sorption element.

As used herein, by "sorbed" it is meant that the volatile delivery enhancing compound is adsorbed on the surface of the sorption element, or absorbed in the sorption element, or both adsorbed on and absorbed in the sorption element.

Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

Preferably, the sorption element is a porous sorption element.

For example, the sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

The size, shape and composition of the sorption element may be chosen to allow a desired amount of volatile delivery enhancing compound to be sorbed on the sorption element.

Preferably, between about 20 µl and about 200 µl, more preferably between about 40 µl and about 150 µl, most preferably between about 50 µl and about 100 µl of the volatile delivery enhancing compound is sorbed on the sorption element.

The sorption element advantageously acts as a reservoir for the volatile delivery enhancing compound.

Preferably, the medicament has a melting point below about 150 degrees Celsius.

Preferably the medicament has a boiling point below about 300 degrees Celsius.

Preferably, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(I-methyl-2-pyrrolidinyl)isoxazole (ABT 418) and (±)-2-(3-Pyridinyl)-I-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

Preferably, the medicament source comprises a nicotine source. The nicotine source may comprise one or more of nicotine, nicotine base, a nicotine salt, such as nicotine-HCl, nicotine-bitartrate, or nicotine-tartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

The nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof The nicotine source may comprise an aqueous solution of nicotine, nicotine base, a nicotine salt or a nicotine derivative and an electrolyte forming compound.

The nicotine source may further comprise other components including, but not limited to, natural flavours, artificial flavours and antioxidants.

The medicament source may comprise a sorption element as described above and a medicament sorbed on the sorption element. The medicament may be sorbed onto the sorption element during manufacture and the sorption element may be sealed. Alternatively, the medicament may be stored separately from the sorption element, for example in a blister on or adjacent the sorption element.

The aerosol-generating device may be configured to heat the medicament source and the volatile delivery enhancing compound source of the aerosol-generating article so that the medicament source of the aerosol-generating article has a higher temperature than the volatile delivery enhancing compound source of the aerosol-generating article. The aerosol-generating device may be configured to substantially simultaneously heat the medicament source and the volatile delivery enhancing compound source of the aerosol-generating article.

The aerosol-generating device and the aerosol-generating article may be configured to heat the medicament source to a first temperature and to heat the volatile delivery enhancing compound source to a second temperature, wherein the first temperature is at least about 50 degrees Celsius higher than the second temperature, preferably at least about 70 degrees Celsius higher than the second temperature, most preferably at least about 80 degrees Celsius higher than the second temperature. Additionally, or alternatively, the first temperature is preferably no more than about 100 degrees Celsius higher than the second temperature. Preferably, the temperature difference between the first and second temperatures is between about 50 and about 100 degrees Celsius, more preferably between about 60 and about 100 degrees Celsius, most preferably between about 80 and about 100 degrees Celsius.

The aerosol-generating device and the aerosol-generating article may be configured to heat the volatile delivery enhancing compound source to a temperature of at least about 30 degrees Celsius. Additionally, or alternatively, the aerosol-generating device and the aerosol-generating article may be configured to heat the volatile delivery enhancing compound source to a temperature of less than about 100 degrees Celsius, preferably less than about 70 degrees Celsius. Preferably, the aerosol-generating device and the aerosol-generating article are configured to heat the volatile delivery enhancing compound source to a temperature of between about 30 and about 100 degrees Celsius, more preferably between about 30 and about 70 degrees Celsius.

The aerosol-generating device and the aerosol-generating article may be configured to heat the medicament source to a temperature of at least about 50 degrees Celsius. Additionally, or alternatively, the aerosol-generating device and the aerosol-generating article may be configured to heat the medicament source to a temperature of less than about 150 degrees Celsius, preferably less than about 100 degrees Celsius. Preferably, the aerosol-generating device and the aerosol-generating article are configured to heat the medicament source to a temperature of between about 50 and about 150 degrees Celsius, more preferably between about 50 and about 100 degrees Celsius.

The aerosol-generating device may further comprise a controller configured to control a supply of power to the heater element.

The aerosol-generating device may further comprise a power supply for supplying power to the heater element and a controller configured to control a supply of power from the power supply to the heater element. The controller of the aerosol-generating device may be configured to control a supply of power from an external power supply to the heater element.

The heater element may be an electric heater element powered by an electric power supply. Where the heater element is an electric heater element, the aerosol-generating device may further comprise an electric power supply and a controller comprising electronic circuitry configured to control the supply of electric power from the electric power supply to the electric heater element.

The power supply may be a DC voltage source. The power supply may be a battery. The power supply may be a Nickel-metal hydride battery, a Nickel cadmium battery, or a Lithium based battery, for example a Lithium-Cobalt, a Lithium-Iron-Phosphate or a Lithium-Polymer battery. The power supply may be another form of charge storage device such as a capacitor. The power supply may require recharging and may have a capacity that allows for the storage of enough energy for use of the aerosol-generating device with one or more aerosol-generating articles.

The heater element may be a non-electric heater, such as a chemical heating means.

The heater element of the aerosol-generating device preferably comprises a single heater element to simplify the construction of the aerosol-generating device. Differential heating of the medicament source and the volatile delivery enhancing compound source may be achieved by contacting at least one of the sources with the resilient member, which in turn is biased against the heater element.

The heater element may have any suitable shape. Preferably, the heater element is an elongate heater element. Preferably, the elongate heater element has a width that is greater than the thickness of the heater element so that the heater element forms a heater blade.

Preferably, the heater element is heated electrically. However, other heating schemes may be used to heat the heater element. The heater element may be heated by conduction from another heat source. The heater element may comprise an infra-red heater element, a photonic source, or an inductive heater element.

The heater element may comprise a heat sink, or heat reservoir comprising a material capable of absorbing and storing heat and subsequently releasing the heat over time to the aerosol-forming article. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, a metal salt, a mixture of eutectic salts or an alloy.

The heater element preferably comprises an electrically resistive material. The heater element may comprise a non-elastic material, for example a ceramic sintered material, such as alumina ($Al_2O_3$) and silicon nitride ($Si_3N_4$), or printed circuit board or silicon rubber. Alternatively, the heater element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required.

The aerosol-generating device may comprise one or more temperature sensors configured to sense the temperature of at least one of the heater element, the medicament source and the volatile delivery enhancing compound source. The controller may be configured to control a supply of power to the heater element based on the sensed temperature.

The heater element may be formed using a metal having a defined relationship between temperature and resistivity. The metal may be formed as a track between two layers of suitable insulating materials. A heater element formed in this manner may be used both as a heater and a temperature sensor.

The invention will now be further described, by way of example only, with reference to the accompanying drawings in which.

Figure 10:
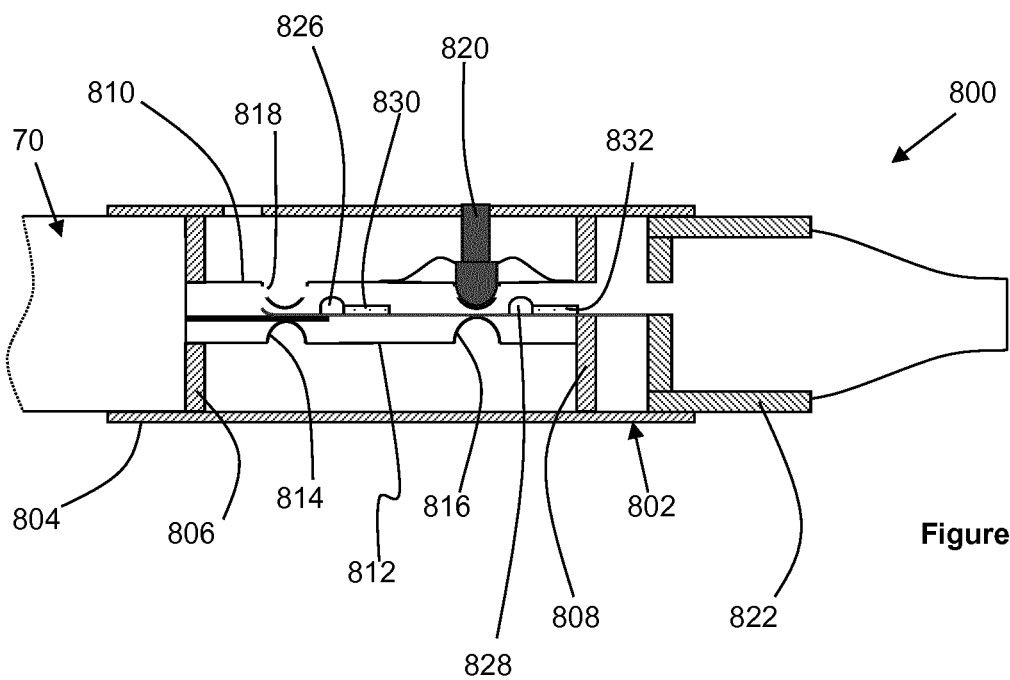
Figure 11:
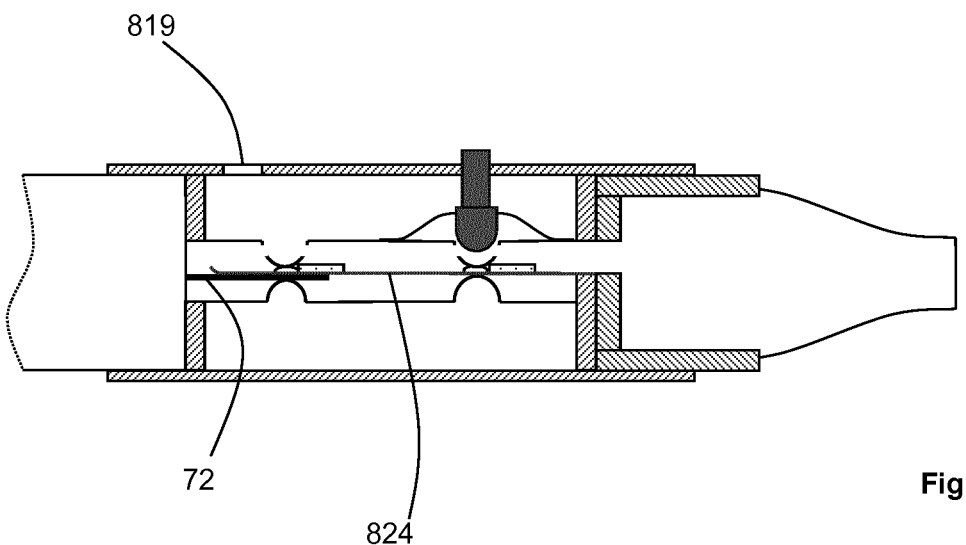

FIG. 10 shows an aerosol-generating system in accordance with the fourth set of embodiments of the present invention, before activation of the aerosol-generating article and with an airflow passage through the aerosol-generating article in a closed state; and FIG. 11 shows the aerosol-generating system of FIG. 10 after activation of the aerosol-generating article and with the airflow passage through the aerosol-generating article in an open state.

Like reference numerals will be used to designate like parts in the following description of the drawings.

Figure 1:
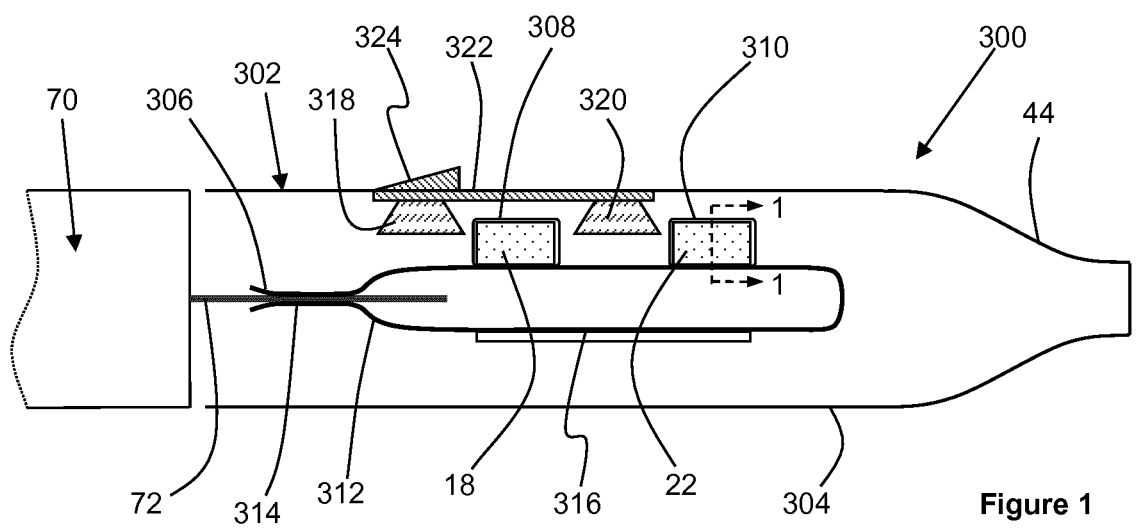
FIG. 1 shows an aerosol-generating system in accordance with the first set of embodiments of the present invention.

FIG. 1 shows an aerosol-generating system 300 in accordance with the first set of embodiments of the present invention. The aerosol-generating system 300 comprises an aerosol-generating article 302 in combination with an aerosol-generating device 70. The aerosol-generating device 70 comprises heater element 72 in the form of a heater blade. The heater element 72 is electrically heated and the aerosol-generating device may comprise a power source and control electronics, as is known in the art.

The aerosol-generating article 302 comprises an outer housing 304 and a mouthpiece 44. The mouthpiece 44 may be formed integrally with the outer housing 304, or the mouthpiece 44 may be formed separately. The outer housing 304 and the mouthpiece 44 are formed from a thermally insulating material, such as a plastic.

A medicament source 18 and a volatile delivery enhancing compound source 22 are provided on a first resilient member 306. Frangible barriers 308 and 310 formed from a metal foil seal the medicament source 18 and the volatile delivery enhancing compound source 22 respectively. A second resilient member 312 is also provided within the outer housing 304, the first and second resilient members 306 and 312 each having an upstream portion 314 and a downstream portion 316. The upstream portions 314 of the first and second resilient members 306 and 312 are positioned adjacent each other and arranged to grip the heater element 72 of the aerosol-generating device 70 when inserted into the aerosol-generating article 302. The downstream portions 316 of the first and second resilient members 306 and 312 are spaced apart.

In the embodiment shown in FIG. 1, the first and second resilient members 306 and 312 are formed from a single piece of resilient material so that the downstream portions 316 of the resilient member are connected at their downstream ends by a continuous portion of the resilient material. However, the first and second resilient members 306 and 312 can alternatively be formed separately and separately mounted within the outer housing 304.

The resilient members 306 and 312 are formed from a thermally conductive resilient material, such as metal, capable of withstanding the operating temperature of the heater element that contacts the upstream portions 314 of the resilient members 306 and 312 during operation of the system. With the heater element 72 of the aerosol-generating device 70 inserted into the aerosol-generating article 302, the heater element 72 contacts the upstream portions 314 of the resilient members 306 and 312 so that the upstream portions 314 are resiliently biased against the heater element 72.

The aerosol-generating device 302 also comprises a rupturing portion in the form of first and second cutting blades 318 and 320 mounted on a carrier element 322. The carrier element 322 is slidably mounted on the outer housing 304 and comprises a push-button 324 that extends through an elongate slot in the outer housing 304. To activate the aerosol-generating article 302, a user pushes on the push-button 324 to slide the carrier element 322 along the outer housing 304, so that the first and second cutting blades 318 rupture the frangible barriers 308 and 310. The aerosol-generating device 302 may further comprise a resilient biasing element, such as a spring, to return the carrier element 322 to the pre-activation position when the user releases the push-button 324.

During operation of the aerosol-generating system 300, the heater element 72 heats the medicament source 18 and the volatile delivery enhancing compound source 22 via the first resilient member 306. The medicament source 18 is positioned on the first resilient member 306 upstream from the volatile delivery enhancing compound source 22 and therefore closer to the heater element 72. Accordingly, the heater element 72 heats the medicament source 18 to a higher temperature than the volatile delivery enhancing compound source 22.

Figure 2:
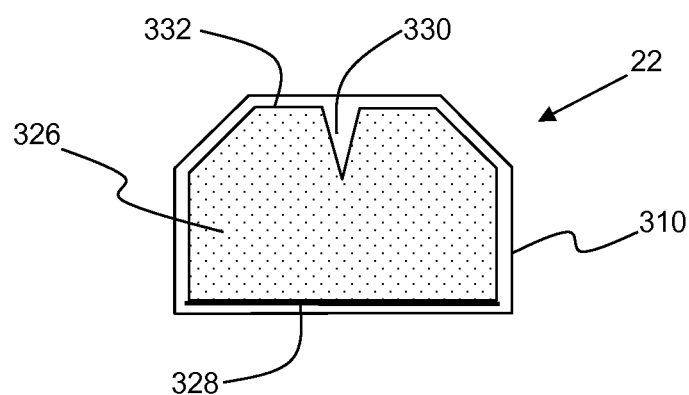
FIG. 2 shows a cross-sectional view of the volatile delivery enhancing compound source of the aerosol-generating system of FIG. 1.

FIG. 2 shows a transverse cross-sectional view of the volatile delivery enhancing compound source 22 taken along line 1-1 in FIG. 1. The volatile delivery enhancing compound source comprises a sorption element 326 onto which the volatile delivery enhancing compound is sorbed. In this embodiment, the sorption element 326 is mounted on a base plate 328 and the entire volatile delivery enhancing compound source is wrapped in the frangible barrier 310. A V-shaped slot 330 is provided in the upper surface 332 of the sorption element 326 and extends along the entire length of the upper surface 332. During activation of the aerosol-generating article 302, the second cutting blade 318 passes along the V-shaped slot 330 to rupture the frangible barrier 310. In this embodiment, the medicament source 18 is constructed in an identical manner to the volatile delivery enhancing compound source 22 and therefore also comprises a V-shaped slot in the upper surface of a sorption element.

Figure 3:
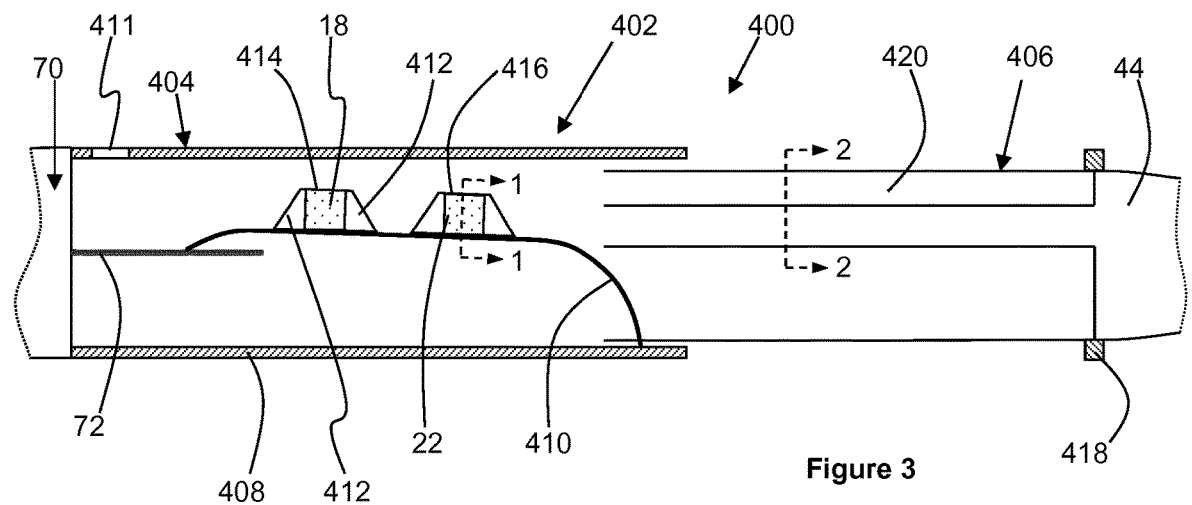
FIG. 3 shows an aerosol-generating system in accordance with the second set of embodiments of the present invention, before activation of the aerosol-generating article.

FIG. 3 shows an aerosol-generating system 400 in accordance with a second embodiment of the present invention. The aerosol-generating system 400 comprises an aerosol-generating article 402 in combination with an aerosol-generating device 70, as described with respect to the previous embodiment.

The aerosol-generating article 402 comprises a housing portion 404 connected to the aerosol-generating device 70 and an insert portion 406 slidably received within a downstream end of the housing portion 404.

The housing portion 404 comprises an outer housing 408, a resilient member 410 connected at its downstream end to the outer housing 408, and an airflow inlet 411 in an upstream end of the outer housing 408. A medicament source 18 and a volatile delivery enhancing compound source 22 are provided on the resilient member 410. Rigid supports 412 are provided adjacent each end of each of the medicament source 18 and the volatile delivery enhancing compound source 22. Frangible barriers 414 and 416 formed from a metal foil seal the medicament source 18 and the volatile delivery enhancing compound source 22 respectively. For ease of constructing the aerosol-generating article 402, preferably the frangible barriers also wrap around the rigid supports 412, as described in more detail below with reference to FIG. 5.

An upstream end of the resilient member 410 is resiliently biased against the heater element 72 of the aerosol-generating device 70. As described with respect to the previous embodiment, the resilient member 410 is formed from a thermally conductive resilient material, such as metal, capable of withstanding the operating temperature of the heater element 72.

The insert portion 406 comprises an annular stopper 418 and a mouthpiece 44, as described previously, extending downstream from the annular stopper 418. Extending upstream from the annular stopper 418 and the mouthpiece 44 is a rupturing portion 420, which is described in more detail below with respect to FIG. 6.

Figure 5:
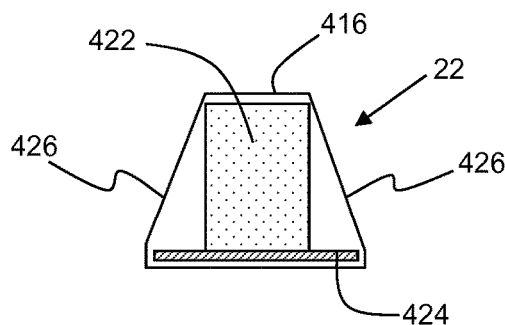
FIG. 5 shows a cross-sectional view of the volatile delivery enhancing compound source of the aerosol-generating system of FIGS. 3 and 4.

FIG. 5 shows a transverse cross-sectional view of the volatile delivery enhancing compound source 22 taken along line 1-1 in FIG. 3. The volatile delivery enhancing compound source comprises a sorption element 422 onto which the volatile delivery enhancing compound is sorbed. The sorption element 422 and the rigid supports 412 at each end of the sorption element 422 are mounted on a base plate 424 and the base plate 424, the rigid supports 412 and the sorption element 422 are wrapped in the frangible barrier 416. The transverse cross-sectional shape of the rigid supports 412 is the same as the transverse cross-sectional shape of the sorption element 422, and the width of the base plate 424 is larger than the width of the sorption element 422 and the rigid supports 412. Therefore, the side portions 426 of the frangible barrier 416 are spaced apart from the sorption element 422 and the rigid supports 412. In this embodiment, the medicament source 18 is constructed in an identical manner to the volatile delivery enhancing compound source 22.

Figure 4:
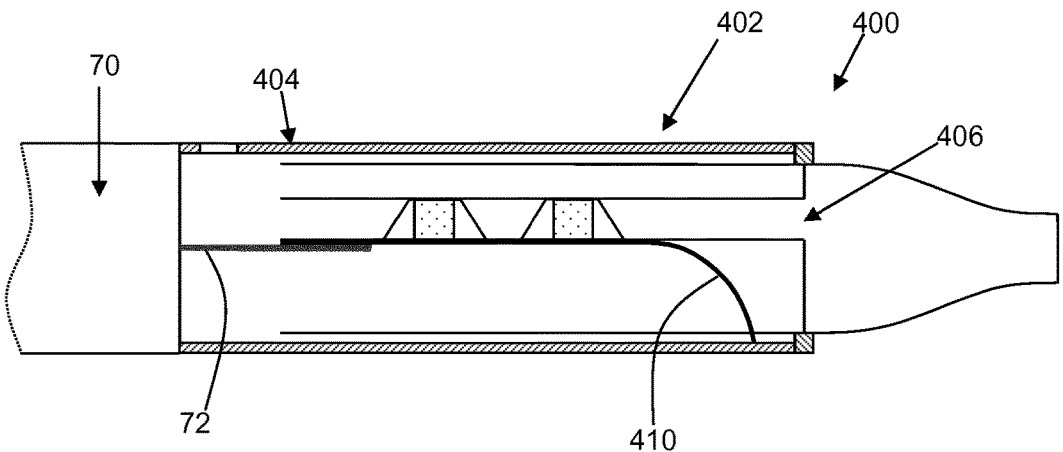
FIG. 4 shows the aerosol-generating system of FIG. 3 after activation of the aerosol-generating article.
Figure 6:
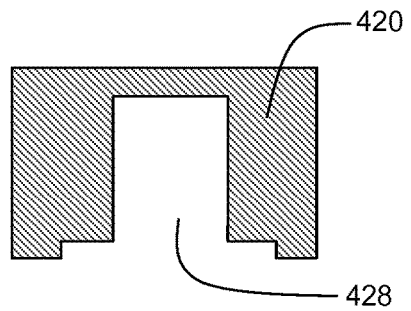
FIG. 6 shows a cross-sectional view of a moveable part of the aerosol-generating system of FIGS. 3 and 4.

FIG. 6 shows a transverse cross-sectional view of the rupturing portion 420 taken along line 2-2 in FIG. 3. As shown by comparing FIGS. 5 and 6, the rupturing portion 420 comprises a longitudinal cut-out 428 having a transverse cross-sectional shape that is slightly larger than the combined transverse cross-sectional shape of the sorption element 422 and the base plate 424. Therefore, to activate the aerosol-generating article 402, a user pushes the insertion portion 406 into the housing portion 404 until the annular stopper 418 abuts the downstream end of the outer housing 408. As the insertion portion 406 slides into the housing portion 404, the rupturing portion 420 pushes against the side portions 426 of the frangible barriers 414 and 416 and therefore ruptures the frangible barriers 414 and 416. At the same time, the rupturing portion 420 further depresses the resilient member 410 against the heater element 72 to ensure optimum contact between the resilient member 410 and the heater element 72, as shown in FIG. 4.

During operation of the aerosol-generating system 400, the heater element 72 heats the medicament source 18 and the volatile delivery enhancing compound source 22 via the resilient member 410. The medicament source 18 is positioned on the resilient member 410 upstream from the volatile delivery enhancing compound source 22 and therefore closer to the heater element 72. Accordingly, the heater element 72 heats the medicament source 18 to a higher temperature than the volatile delivery enhancing compound source 22.

Figure 7:
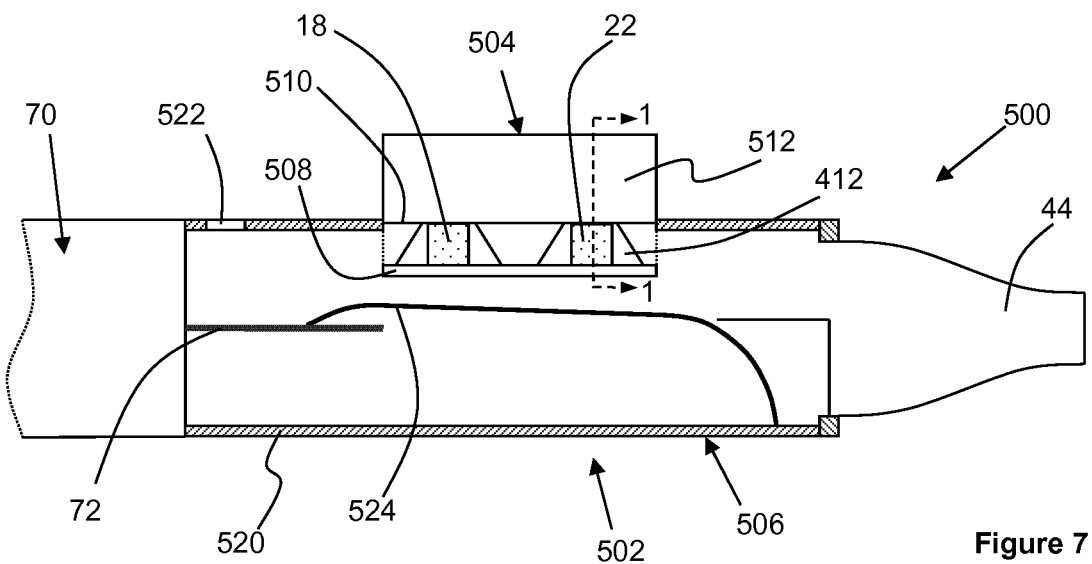
FIG. 7 shows an aerosol-generating system in accordance with the third set of embodiments of the present invention, before activation of the aerosol-generating article.

FIG. 7 shows an aerosol-generating system 500 in accordance with a third embodiment of the present invention. The aerosol-generating system 500 comprises an aerosol-generating article 502 in combination with an aerosol-generating device 70, as described with respect to the previous embodiments.

The aerosol-generating article 502 comprises a consumable portion 504 and a reusable mouthpiece portion 506 that attaches to the aerosol-generating device 70. The consumable portion 504 comprises a medicament source 18 and a volatile delivery enhancing compound source 22, both as described previously. Rigid supports 412 are provided adjacent each end of each of the medicament source 18 and the volatile delivery enhancing compound source 22. The medicament source 18, the volatile delivery enhancing compound source 22 and the rigid supports 412 are mounted on a first wall portion in the form of a common base plate 508. A frangible barrier 510 formed from a metal foil wraps entirely around the medicament source 18, the volatile delivery enhancing compound source 22, the rigid support 412 and the common base plate 508 to seal the medicament source 18 and the volatile delivery enhancing compound source 22.

Figure 9:
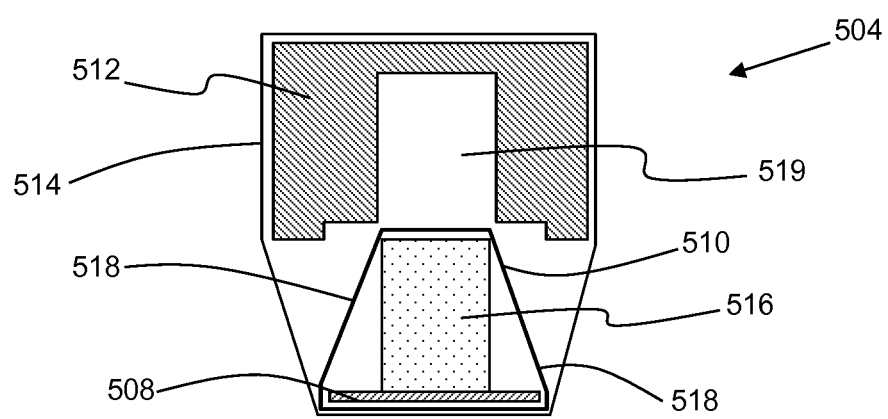
FIG. 9 shows a cross-sectional view of a consumable portion of the aerosol-generating system of FIGS. 7 and 8.

As shown more clearly in FIG. 9, which shows a transverse cross section of the consumable portion 504 taken along line 1-1 in FIG. 7, the consumable portion 504 also comprises a second wall portion in the form of a rupturing portion 512 positioned adjacent the medicament source 18, the volatile delivery enhancing compound source 22 and the rigid supports 412. The rupturing portion 512 is connected to the remainder of the consumable portion 504 by a foil wrap 514 that wraps around the top and sides of the rupturing portion 512 and around the bottom of the common base plate 508. The foil wrap 514 does not extend across the upstream and downstream ends of the consumable portion 504 so that an airflow passage is established through the consumable portion 504.

As shown in FIG. 9, the volatile delivery enhancing compound source 22 comprises a sorption element 516 onto which the volatile delivery enhancing compound is sorbed. In this embodiment, the medicament source 18 comprises a similar sorption element having the same transverse cross-sectional shape as the sorption element 516. The transverse cross-sectional shape of the rigid supports 412 is also the same as the transverse cross-sectional shape of the sorption element 516, and the width of the common base plate 508 is larger than the width of the sorption elements and the rigid supports 412. Therefore, the side portions 518 of the frangible barrier 510 are spaced apart from the sorption elements and the rigid supports 412.

As shown in FIG. 9, the rupturing portion 512 comprises a longitudinal cut-out 519 having a transverse cross-sectional shape that is slightly larger than the combined transverse cross-sectional shape of the sorption elements and the common base plate 508. Therefore, to activate the consumable portion 504, a user pushes the rupturing portion 512 towards the medicament source 18 and the volatile delivery enhancing compound source 22 so that the rupturing portion 512 pushes against the side portions 518 of the frangible barrier 510 and ruptures the frangible barrier 510. To prevent accidental activation of the consumable portion 504, the consumable portion 504 may comprise one or more resilient biasing elements, such as one or more springs, positioned between the rupturing portion 512 and the common base plate 508 to bias the rupturing portion 512 away from the common base plate 508. Additionally, or alternatively, the consumable portion 504 may comprise one or more elements that function to retain the rupturing portion 512 against the common base plate 508 after the consumable portion 504 has been activated. For example, an interference fit between the rupturing portion 512 and the common base plate 508 may retain the rupturing portion 512 against the common base plate 508 after the consumable portion 504 has been activated.

The mouthpiece portion 506 comprises an outer housing 520 and a mouthpiece 44 at a downstream end of the outer housing 520, as described previously. The mouthpiece 44 may be formed integrally with the outer housing 520, or the mouthpiece 44 may be formed separately and attached to the outer housing 520. An airflow inlet 522 at the upstream end of the outer housing 520 establishes an airflow passage through the outer housing 520 from the airflow inlet 522 to the mouthpiece 44.

A resilient member 524 is secured at its downstream end to an inner surface of the outer housing 520. An upstream end of the resilient member 524 is resiliently biased against the heater element 72 of the aerosol-generating device 70. As described with respect to previous embodiments, the resilient member 524 is formed from a thermally conductive resilient material, such as metal, capable of withstanding the operating temperature of the heater element 72.

Figure 8:
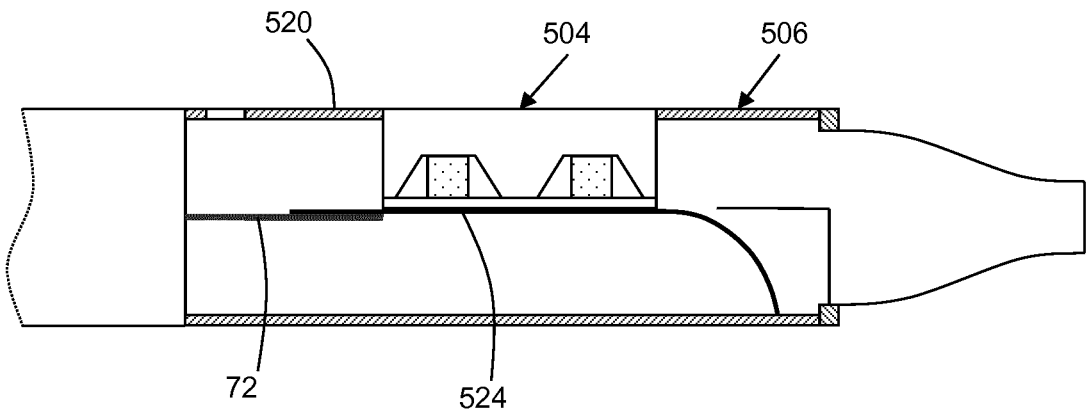
FIG. 8 shows the aerosol-generating system of FIG. 7 after activation of the aerosol-generating article.

To prepare the aerosol-generating system 500 for operation, the consumable portion 504 is inserted into the mouthpiece portion 506 through an aperture in a sidewall of the outer housing 520. Pushing the consumable portion 504 into the mouthpiece portion 506 further depresses the resilient member 524 against the heater element 72 to ensure optimum contact between the resilient member 524 and the heater element 72, as shown in FIG. 8. The consumable portion 504 may be pre-activated by the user, or the action of pushing the consumable portion 504 against the resilient member 524 may activate the consumable portion 504.

During operation of the aerosol-generating system 500, the heater element 72 heats the medicament source 18 and the volatile delivery enhancing compound source 22 via the resilient member 524 and the common base plate 508. For this reason, the common base plate 508 is also constructed from a thermally conductive material, such as a metal. The medicament source 18 is positioned on the common base plate 508 upstream from the volatile delivery enhancing compound source 22 and therefore closer to the heater element 72. Accordingly, the heater element 72 heats the medicament source 18 to a higher temperature than the volatile delivery enhancing compound source 22.

FIGS. 10 and 11 show an aerosol-generating system 800 in accordance with a fourth embodiment of the present invention. The aerosol-generating system 800 comprises an aerosol-generating article 802 and an aerosol-generating device 70, as described previously.

The aerosol-generating article 802 comprises a tubular outer housing 804 in which an upstream annular stopper 806 and a downstream annular stopper 808 are mounted. Extending between the annular stoppers 806 and 808 are a first rupturing portion 810 and a second rupturing portion 812 each comprising an elongate plate having an upstream protrusion 814 and a downstream protrusion 816. The protrusions 814 and 816 on the first rupturing portion 810 each comprise one or more airflow apertures 818 to allow airflow to enter the space between the first and second rupturing portions 810 and 812. An airflow inlet 819 in the outer housing 804 allows air to flow into the aerosol-generating article 802.

A push-button 820 shaped for insertion into the recess forming the downstream protrusion 816 on the first rupturing portion 810 extends through an aperture in the outer housing 804. The push-button 820 allows a user to selectively block and unblock the airflow apertures 818 in the upstream protrusion of the first rupturing portion 810 to prevent or allow the flow of air through the aerosol-generating article 802 after the aerosol-generating article 802 has been activated. The push-button 820 is shown in the blocked position in FIG. 10 and the unblocked position in FIG. 11.

The aerosol-generating article 802 further comprises a tubular segment 822 slidably received within the downstream end of the outer housing 804. A mouthpiece 44, as described previously, extends downstream from the tubular segment 822. A resilient member 824 extends upstream from the tubular segment 822 and is positioned between the first and second rupturing portions 810 and 812. The resilient member 824 is resiliently biased against the heater element 72 of the aerosol-generating device 70. As described with respect to previous embodiments, the resilient member 824 is formed from a thermally conductive resilient material, such as a metal, capable of withstanding the operating temperature of the heater element 72.

A medicament source in the form of a medicament blister 826 is provided on the resilient member 824, the medicament blister 826 comprising a blister containing a liquid medicament. The blister forms a frangible barrier containing the liquid medicament. Similarly, a volatile delivery enhancing compound source in the form of a volatile delivery enhancing compound blister 828 is provided on the resilient member 824, the volatile delivery enhancing compound blister 828 comprising a blister containing a liquid volatile delivery enhancing compound. The blister forms a frangible barrier containing the liquid volatile delivery enhancing compound. First and second sorption elements 830 and 832 are provided on the resilient member 824 adjacent the medicament and volatile delivery enhancing compound blisters 826 and 828 respectively.

To activate the aerosol-generating article 802, a user slides the tubular segment 822 into the outer housing 804 until the tubular segment abuts the downstream annular stopper 808. Sliding the tubular segment 822 into the outer housing 804 also slides the resilient member 824 further into the housing outer 804 so that the medicament and volatile delivery enhancing compound blisters 826 and 828 are crushed and ruptured between the upstream and downstream protrusions 814 and 816 of the first and second rupturing portions 810 and 812, as shown in FIG. 11. Rupturing the blisters causes at least some of the medicament and the volatile delivery enhancing compound source to be sorbed onto the first and second sorption elements 830 and 832 respectively.

During operation of the aerosol-generating system 800, the heater element 72 heats the medicament source and the volatile delivery enhancing compound source via the resilient member 824. The medicament source is positioned on the resilient member 824 upstream from the volatile delivery enhancing compound source and therefore closer to the heater element 72. Accordingly, the heater element 72 heats the medicament source to a higher temperature than the volatile delivery enhancing compound source.

The invention claimed is:

1. An aerosol-generating system, comprising:
an aerosol-generating device comprising a heater element; and
an aerosol-generating article configured to engage with the aerosol-generating device and comprising:
a consumable comprising:
a medicament source,
a volatile delivery enhancing compound source,
a first wall portion on which the medicament source and the volatile delivery enhancing compound source are disposed,
a second wall portion comprising a rupturing portion, the second wall portion being connected to the first wall portion and configured for relative sliding movement between the first and second wall portions, and
at least one frangible barrier sealing the medicament source and the volatile delivery enhancing compound source, wherein the at least one frangible barrier is disposed between the first and second wall portions; and
a mouthpiece portion configured for attachment to the aerosol-generating device and comprising an aperture configured to receive the consumable,
wherein the aerosol-generating article is configured so that inserting the consumable into the aperture in the mouthpiece portion results in relative movement between the first and second wall portions so that the rupturing portion ruptures the at least one frangible barrier.

2. The aerosol-generating system according to claim 1, wherein the heater element comprises an elongate heater element,
wherein the aerosol-generating article further comprises a resilient member disposed within the mouthpiece portion, and
wherein the aerosol-generating article is configured so that inserting the consumable into the mouthpiece portion biases the resilient member against the elongate heater element when the mouthpiece portion is attached to the aerosol-generating device.

* * * * *